(12) United States Patent
McDaniel et al.

(10) Patent No.: US 7,588,166 B2
(45) Date of Patent: Sep. 15, 2009

(54) DISPENSER FOR PERSONAL CARE ABSORBENT ARTICLES

(75) Inventors: Mary L. McDaniel, Appleton, WI (US); Herb F. Velazquez, Neenah, WI (US); William Reeves, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1149 days.

(21) Appl. No.: 10/732,925

(22) Filed: Dec. 10, 2003

(65) Prior Publication Data
US 2005/0127084 A1 Jun. 16, 2005

(51) Int. Cl.
*B65H 1/00* (2006.01)
(52) U.S. Cl. .............................. 221/33; 221/155; 221/64
(58) Field of Classification Search .................... 221/33, 221/37–39, 45–49, 62–63, 197–198, 208–209, 221/270–271, 279–280
See application file for complete search history.

(56) References Cited

U.S. PATENT DOCUMENTS

| | | | | |
|---|---|---|---|---|
| 2,604,205 | A | * | 7/1952 | Patterson ...................... 221/52 |
| 3,343,716 | A | * | 9/1967 | Peebles ........................ 221/46 |
| 3,446,395 | A | | 5/1969 | Ballin |
| 4,005,776 | A | | 2/1977 | Seeley |
| 4,119,203 | A | | 10/1978 | Kuchenbecker |
| 4,210,246 | A | | 7/1980 | Kuchenbecker |
| 4,354,619 | A | * | 10/1982 | Wippermann et al. ....... 221/263 |
| 4,905,869 | A | | 3/1990 | Grigsby et al. |
| 4,938,462 | A | | 7/1990 | Gould |
| 5,143,218 | A | | 9/1992 | Brauckmann |
| 5,154,293 | A | | 10/1992 | Gould |
| 5,197,631 | A | * | 3/1993 | Mishima ....................... 221/52 |
| 5,293,997 | A | | 3/1994 | Hustad et al. |
| 5,297,679 | A | | 3/1994 | Rondone et al. |
| 5,467,893 | A | * | 11/1995 | Landis et al. ................. 221/34 |

(Continued)

FOREIGN PATENT DOCUMENTS

CA 2354650 1/2003

(Continued)

OTHER PUBLICATIONS

US 5,699,911, 12/1997, Joseph et al. (withdrawn)

*Primary Examiner*—Gene Crawford
*Assistant Examiner*—Michael K Collins
(74) *Attorney, Agent, or Firm*—Dority & Manning, P.A.

(57) ABSTRACT

A portable carrying case for personal care absorbent articles, particularly feminine hygiene care products, includes a body defining an internal enclosure for receipt of a plurality of the stacked personal care absorbent articles. An opening is defined in the body at a location so as to expose an upper one of the absorbent articles for dispensing without generally exposing underlying absorbent articles. A lid is movably disposed relative to body from a closed position to an open position wherein access is provided to the absorbent articles through the opening. A manual push structure is defined in the body generally opposite from the opening. The push structure allows a user to push on the bottommost one of the stacked absorbent articles so as to move the uppermost one of the stack of articles towards the opening for grasping and retrieval by the user. A biasing element may bias the articles towards the push structure.

31 Claims, 3 Drawing Sheets

U.S. PATENT DOCUMENTS

| | | | |
|---|---|---|---|
| 5,595,300 A | | 1/1997 | Paik et al. |
| 5,704,471 A | * | 1/1998 | Yamada .................... 206/207 |
| 5,775,516 A | | 7/1998 | McCumber et al. |
| 6,152,322 A | * | 11/2000 | Marino ....................... 221/63 |
| 6,158,614 A | * | 12/2000 | Haines et al. ............... 221/63 |
| 6,247,590 B1 | | 6/2001 | Baker |
| 6,349,849 B1 | * | 2/2002 | Pehr ........................... 221/33 |
| 6,604,651 B2 | * | 8/2003 | Amundson et al. ........... 221/47 |
| D485,749 S | * | 1/2004 | Zaksenberg et al. ......... D9/424 |
| 6,799,695 B1 | * | 10/2004 | Borrero ....................... 221/59 |
| 2005/0173450 A1 | * | 8/2005 | Maskell et al. .............. 221/186 |

FOREIGN PATENT DOCUMENTS

| | | |
|---|---|---|
| FR | 683663 | 3/1930 |
| WO | 03037746 | 5/2003 |

* cited by examiner

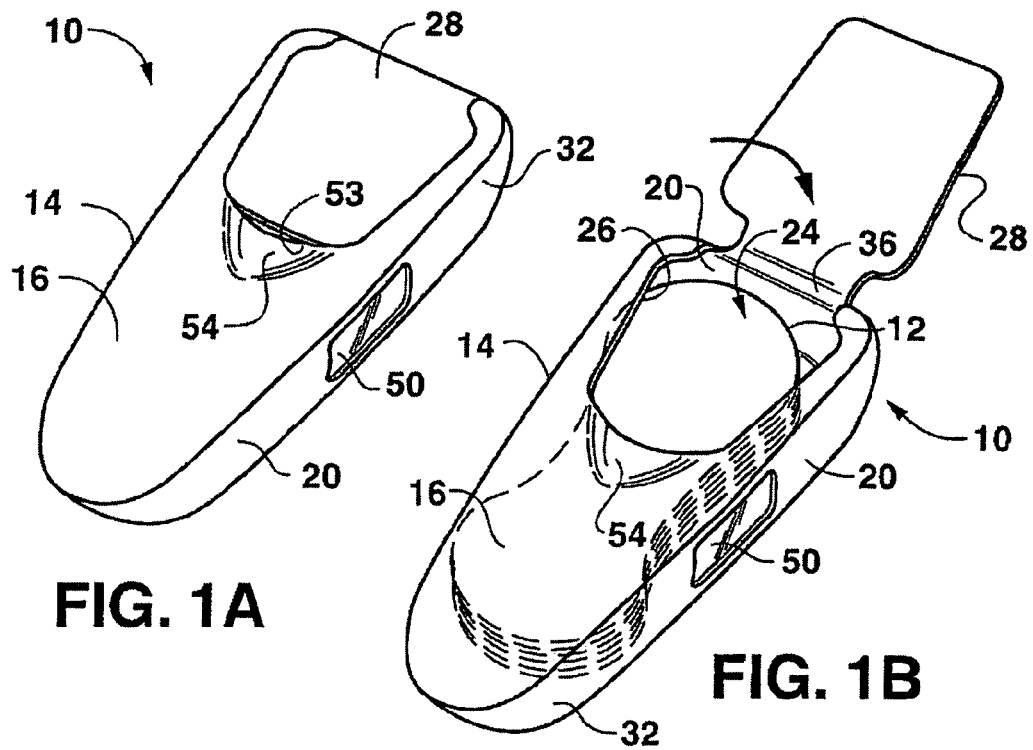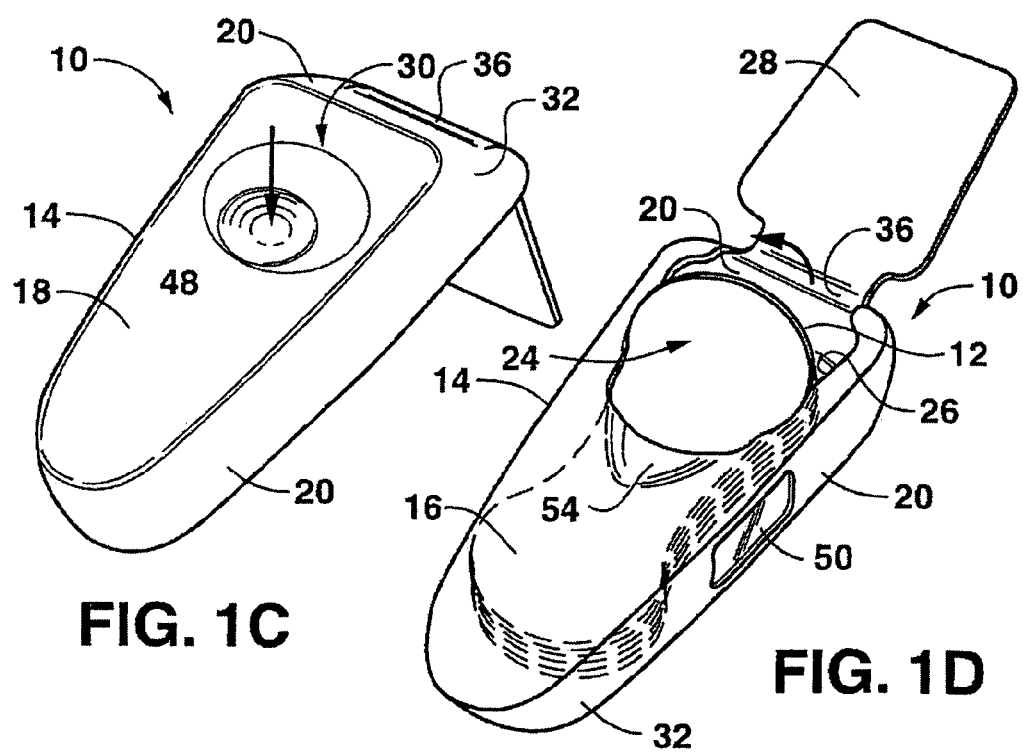

DISPENSER FOR PERSONAL CARE ABSORBENT ARTICLES

FIELD OF THE INVENTION

The present invention relates generally to the field of disposable absorbent articles, and more particularly to an apparatus for storing and dispensing absorbent articles such as feminine care articles.

BACKGROUND

Disposable feminine hygiene absorbent articles are well known and include, for example, sanitary napkins, pantiliners, tampons, interlabial devices, and the like. The industry is continuously seeking improvements and advances in such articles and, in general, has been successful in providing consumers with reliable and comfortable products that perform well for their intended purpose.

Although much focus has been given to the actual absorbent articles themselves, the packaging, storing, and dispensing of such articles can still be problematic. The articles typically end up loosely deposited in a women's purse, handbag, carrying case, and so forth, such that the exercise of locating the article when needed can be frustrating. Also, most individuals value their privacy and prefer not to advertise to others that they have or are using personal care products by, for example, having to take their purse or carrying case to the restroom. Additionally, many types of conventional products are individually wrapped and sealed in a film material. Even if the woman can discretely carry and easily locate the product, the act of opening the wrapped package and retrieving the article can be relatively noisy due to the nature of the film material and sealing methods employed to seal the edges of the package. This noise may be another point of embarrassment for the consumer.

Accordingly, a need exist for an improved system for allowing consumers to discretely carry, dispense, and use personal care products, particularly feminine care products. The present invention provides a solution to this need.

SUMMARY

Objects and advantages of the invention will be set forth in part in the following description, or may be obvious from the description, or may be learned through practice of the invention.

Although the present invention has particular usefulness in the field of feminine care articles such as shields, pantiliners, sanitary napkins, tampons, and so forth, it should be appreciated that any manner of personal care absorbent article may benefit from the invention, including incontinence articles, and the like. All such uses are within the scope and spirit of the invention. For ease of description only, the working environment of the invention is assumed to be feminine care sanitary napkins or pantiliners.

In accordance with the invention, a portable carrying case for personal care absorbent articles, such as feminine care articles, is provided. The carrying case includes a body that defines an internal enclosure for receipt of a stack of the personal care absorbent articles. The body is not limited by its shape, materials, or configuration, so long as it is appropriate for retaining the stack of absorbent articles. For example, in a particular embodiment, the body may be molded as an integral plastic body having a shape generally conforming to the shape of the articles intended to be placed in the body.

An opening is defined in the body at a location so as to expose an upper one of the absorbent articles for dispensing without generally exposing the underlying absorbent articles. For example, the opening may be defined in a front face or wall of the body such that essentially only the topmost article is exposed. The opening has a size and shape sufficient to allow a user to grasp the exposed article and pull the article from the body.

A lid for the opening is provided and is movably disposed relative to the body from a closed position wherein the opening is covered by the lid, to an open position wherein access is provided to the absorbent articles through the opening. The type of lid and opening mechanism for the lid are not limiting features. For example, the lid may be made of the same material as the body and be pivotally, or slidably mounted to the body to provide access to the opening.

A manual push structure is defined in the body at a location generally opposite from the opening. The push structure may take on various forms and functions to allow a user to push on the bottommost one of the stacked absorbent articles so as to move the uppermost one of the stack of absorbent articles towards the opening so that the user may easily grasp and remove the uppermost article form the body. In a particular embodiment, the push structure is defined by an access opening defined through a wall of the body. The access opening has a restricted size so as to discourage attempts to remove articles from the body through this access opening. To ensure cleanliness of the bottommost article, it may be desired to cover the access opening with any suitable resilient or elastic material, for example a clear or translucent elastic film.

In still an alternate embodiment, the push structure may be defined by a resilient integral region or portion of the back wall of the case, such as a thinned section of the wall.

In a particular embodiment, the carrying case may be a multi-sided structure, such as an elongated structure having a front wall, side walls, and a back wall. The opening may be defined in the front wall and the push structure defined in the oppositely facing back wall. The side walls may define a closed border or perimeter around the enclosure in both the open and closed positions of the lid such that the absorbent articles cannot be slid out of the body intentionally or unintentionally, but must generally be removed by a pulling on the uppermost article in a direction generally transverse to a plane of the opening. For example, in the embodiment wherein the opening is in the front wall of the body, the article is pulled in a direction away from the front wall to remove the article from the body.

It may be desired to provide a viewing window in the body so that a user can ascertain the type and remaining number of articles in the body without opening the lid. In this regard, the window may be defined in a side wall of the body such that the number of articles in the stack can be readily determined. In an alternate embodiment, the window feature may be incorporated with the manual push structure. For example, as described above, the push structure may be an access opening covered by a resilient and translucent material.

It may also be desired to incorporate a biasing structure with the body to bias the stacked absorbent articles generally away from the opening and towards the push structure. In this way, as the number of articles is depleted, the remaining articles will be held securely in the body and will not have a tendency to slip or inadvertently fall out upon opening the lid and turning the body over, and so forth. This biasing structure may be, for example, a relatively simple resilient detent formed in the front surface of the body. The detent may be incorporated into the lid structure. Other resilient or spring-type structures are also suitable for this purpose.

Aspects of the invention will described below in greater detail by reference to particular embodiments, examples of which are illustrated in the figures.

BRIEF DESCRIPTION OF THE FIGURES

FIG. 1A is a perspective view of an embodiment of a portable absorbent article carrying case according to the invention.

FIG. 1B is a perspective view of the embodiment of FIG. 1 with the lid in an open position.

FIG. 1C is perspective view of the back side of the case illustrated in FIG. 1.

FIG. 1D is perspective front view of the case illustrated in FIG. 1 particularly illustrating the removal direction of the absorbent articles.

DETAILED DESCRIPTION

Figure 2:
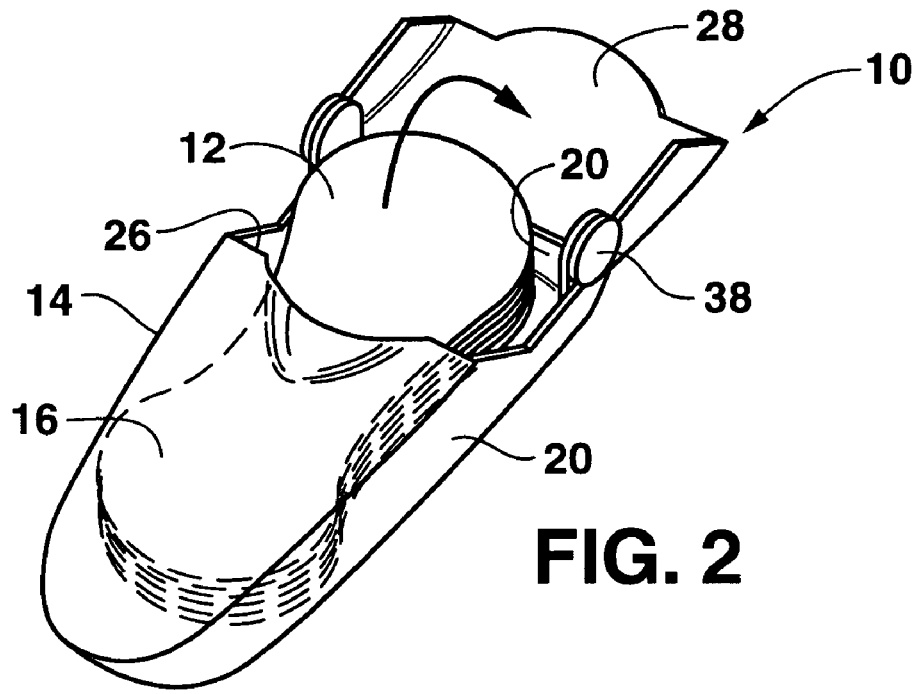
FIG. 2 is a perspective view of an alternate embodiment of a carrying case according to the invention.

The invention will now be described in detail with reference to particular embodiments thereof. The embodiments are provided by way of explanation of the invention, and are not meant as a limitation of the invention. For example, features described or illustrated as part of one embodiment may be used with another embodiment to yield still a further embodiment. It is intended that the present invention include these and other modifications and variations as come within the scope and spirit of the invention.

Referring to the Figures, in which like numerals indicate like parts throughout the several views, embodiments of a portable carrying case 10 are depicted. The case 10 is configured particularly for storage, transport, and dispensing of personal care absorbent protects, for example feminine care absorbent articles such as the sanitary napkins 12 illustrated in the figures. It should be understood, however, that the invention is not limited to use with any particular type of absorbent article, and that the sanitary napkins 12 are depicted for purposes of illustration only. Also, the construction and materials used in conventional absorbent articles, particularly feminine care articles, are well known to those skilled in the art and a detailed description of such articles is not necessary for purposes of explaining the present inventive carrying case 10.

Referring to the figures in general, the carrying case 10 includes a body 14 that defines an internal storage space or enclosure 24 for receipt of a stack of the personal care absorbent articles 12. The body 14 is not limited by its shape, materials, or configuration, so long as it is appropriate for retaining the stack of absorbent articles 12. For example, in a particular embodiment, the body 14 may be molded as an integral plastic body having a shape generally conforming to the shape of the articles 12 intended to be placed in the body 14. The body 14 may have a generally nondescript appearance so that it gives no indication of the absorbent articles 12 carried therein. Alternatively, the body may be relatively ornate or decorative. The body 14 may have an ergonomic shape designed to conform to the hand of the user. A vast number of body 14 configurations are within the scope and spirit of the invention.

In the illustrated embodiment, the body 14 is a relatively thin elongated structure defined by a front wall 16, a back wall 18, and a circumferential side wall 20. The elongated shape of the body 14 generally conforms to the length and shape of the articles 12, as depicted in the figures.

An opening 26 is defined in the body 14 at a location so as to expose an upper one of the absorbent articles 12 for dispensing without generally exposing the underlying absorbent articles. For example, the opening 26 may be defined in the front wall 16 as illustrated such that essentially only the topmost article 12 is exposed by the opening 26. The opening 26 has a size and shape sufficient to allow a user to grasp the exposed article 12 and pull the article from the body 14 in the direction depicted in FIG. 1D. The side wall 20 is generally continuous around the enclosure 24 such that it defines a closed perimeter 32 around the opening 26. In this manner, the articles 12 cannot inadvertently slide out of the enclosure 24, but must be removed from the body 14 by being pulled in a direction generally transverse to a plane of the opening 26.

A lid 28 is provided for the opening 26. The lid 28 is movably disposed relative to the body 14 from a closed position illustrated in FIG. 1A to the open position illustrated in FIGS. 1B and 1D. In the open position of the lid 28, access is provided to the absorbent articles 12 through the opening 26. It should be appreciated that the type of lid 28 and opening mechanism for the lid 28 are not limiting features of the invention. For example, as illustrated in FIGS. 1A through 1D, the lid 28 may be made of the same material as the body 14 and be pivotally mounted to the body 14 to provide access to the opening 26. The lid 28 may be integrally molded with the body 14 and connected to the body by a living hinge 36 that provides the pivotal mechanism between the lid 28 and body 14. The lid 28 may be biased to the closed position by the living hinge 36, or any other type of resilient biasing device, including spring devices. As shown in FIG. 2 for example, the lid 28 may be a separately molded part that is integrally connected to the body 14 by a mechanically pivoting hinge 38 that provides the pivotal mechanism between the lid 28 and body 14.

Figure 3:
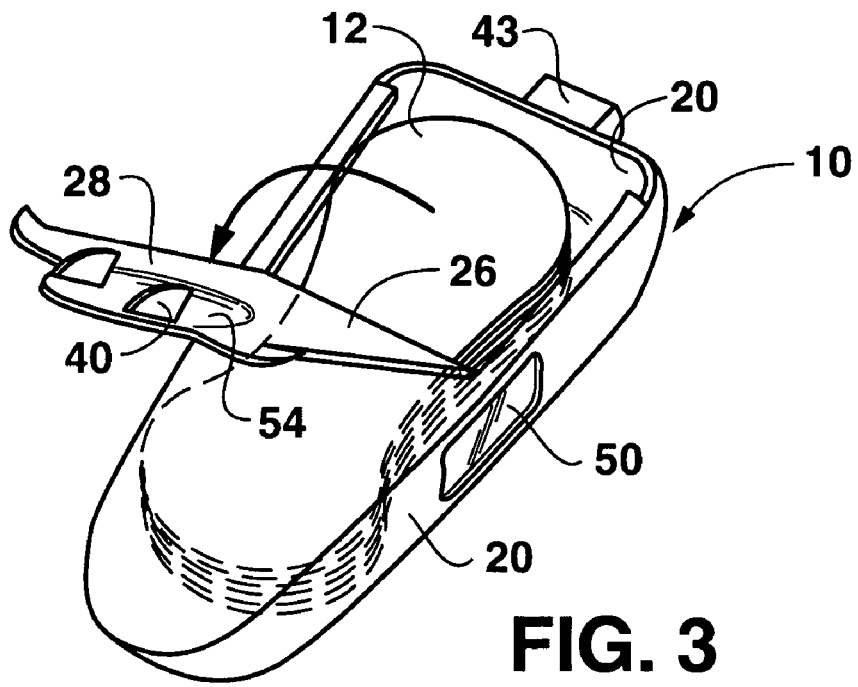
FIG. 3 is a perspective view of still another embodiment of a carrying case according to the invention.

The lid 28 may open away from the body 14, as with the embodiments of FIGS. 1A-1D, and FIG. 2, or towards the body 14, as with the embodiment of FIG. 3.

Figures 4A, 4B:
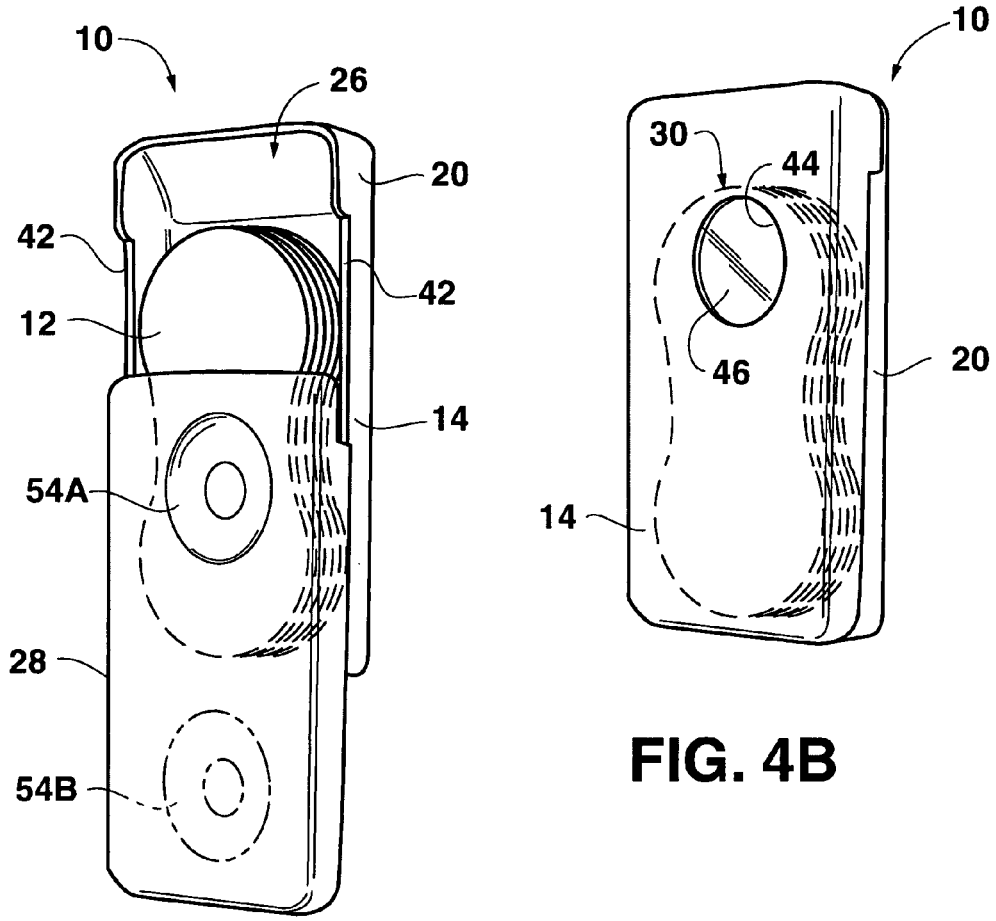
FIG. 4A is a perspective view of an embodiment of a case having a slidable lid in the open position.
FIG. 4B is back view of the embodiment of FIG. 4A.

In the embodiment of FIG. 4A, the lid 28 is a separate component slidably disposed relative to the body 14 on slide tracks 42 to at least partially expose the articles 12 through the opening 26. Structural stops may be formed or otherwise provided along the slide tracks 42 to define (i.e., limit) the range of slidability of the lid 28 and thus ensure that the articles 12 cannot inadvertently fall out of the body 14.

Any conventional locking mechanism may be provided to secure the lid 28 relative to the body 14. In the embodiment of FIG. 3, the locking mechanism is defined by tabs 40 extending inwardly from the lid 28. The tabs 40 frictionally engage on either side of a locking hub 43 provide on the side wall 20 of the body. It should be understood that this embodiment is illustrative only, and that number of mechanical or adhesive locking devices may be utilized to releasably secure the lid 28 to the body 14.

A manual push structure 30 is defined in the body 14 at a location generally opposite from the opening 26. The function of the push structure 30 is to allow a user to push on the bottommost one of the stacked absorbent articles 12 so as to move the uppermost one of the stack of absorbent articles 12 towards the opening 26. In this way, the user may easily grasp and remove the uppermost article 12 form the body 14 without having to "dig" for the article. The push structure 30 may take on various configurations for achieving this purpose. In a relatively simple embodiment illustrated in FIG. 1C, the push structure 30 is defined by resilient integral region or portion 48 of the back wall 14, such as a thinned section of the wall 14. With this embodiment, the user simply presses against the resilient portion 40 from behind to move the uppermost article 12 into a position for easy grasping and removal, as depicted in FIG. 1D.

In an alternate embodiment illustrated in FIG. 4B, the push structure 30 is defined by an access opening 44 defined in the back wall 18. The opening may be uncovered an provide direct limited access to the articles 12. Desirably, the opening 44 has a restricted size so as to discourage attempts to remove articles 12 from the body through the opening 44. To ensure cleanliness of the bottommost article, it may be desired to cover the access opening 44 with any suitable resilient or elastic material 46, for example a clear or translucent elastic film. The film may be adhered to the back wall 18 from within the enclosure 24 so that it cannot readily be peeled from the body 14.

It may be desired to provide a viewing window 50 in the body 14 so that a user can ascertain the type and remaining number of articles 12 in the body 14 without opening the lid. In this regard, the window 50 may be defined in the side wall 20 of the body such that the number of articles in the stack can be readily determined, as illustrated in FIGS. 1A-1D and FIG. 3. The window 50 may be defined by an uncovered opening or, desirably, an opening having a clear or translucent covering or pane. In an alternate embodiment, the window 50 may be incorporated with the manual push structure 30. For example, as described above, the push structure 30 may be an access opening 44 covered by a resilient and translucent film material 46.

It may also be desired to incorporate a biasing structure with the body 14 to bias the stacked absorbent articles 12 generally away from the opening 26 and towards the back wall 18 of the body 14. In this way, as the number of articles 12 is depleted, the remaining articles will be held securely in the body 14 and will not have a tendency to slip or inadvertently fall out upon opening the lid 28 and turning the body over, and so forth. This biasing structure may be any type of resilient or spring device, such as a spring clip, and so forth. In the illustrated embodiments, the biasing structure is provided by a relatively simple resilient detent 54 formed in the front wall 16 of the body 14. This detent 54 may also function to expose a lip region 53 of the lid 28 for easier opening of the lid. In an alternate embodiment as illustrated in FIG. 4A, the detent 54a may be incorporated into the lid structure 28 so as to also aid the user in opening the lid 28 by providing a region for the user to apply a sliding force to the lid. In an alternate embodiment, the detent may be closer towards the bottom of the lid, as illustrated by the dashed line detent 54b in FIG. 4A. In this embodiment, the user can hold the case 10 in the palm of one hand with their thumb on the top of the lid 28 in the detent 54b. The lid 28 may then be slid open by the user simply pushing the detent 54b towards their body while sliding the base 14 in the opposite direction with the other fingers.

It should be appreciated by those skilled in the art that various modifications and variations can be made to the embodiments of the absorbent article described herein without departing from the scope and spirit of the invention as set forth in the appended claims and equivalents thereof.

What is claimed is:

1. A portable carrying case for personal care absorbent articles, comprising:
  a body, said body defining an internal enclosure for receipt of a plurality of stacked personal care absorbent articles, said body configured with an exterior surface that is ergonomically shaped to generally conform to being carried and held in one hand of the user while the user's other hand removes an article from the internal enclosure;
  an opening defined in said body at a location so as to at least partially expose an upper one of said absorbent articles for dispensing without generally exposing underlying absorbent articles;
  a lid movably disposed relative to said body from a closed position wherein said opening is covered by said lid to an open position wherein access is provided to said absorbent articles through said opening; and
  a manual push structure defined in said body generally opposite from said opening, said push structure configured to allow a user to push on the bottommost one of said stacked absorbent articles so as to move the uppermost one of said stack of absorbent articles towards said opening for grasping and retrieval by the user.

2. The absorbent article carrying case as in claim 1, wherein said body comprises a multi-sided structure including a first wall and a second wall disposed opposite said first wall, said opening defined in said first wall and said push structure defined in said second wall.

3. The absorbent article carrying case as in claim 2, wherein said multi-sided structure comprises a front wall, a back wall, and circumferential sides walls so as to define an elongated box-like structure, said opening defined in said front wall and said push structure defined in said back wall.

4. The absorbent article carrying case as in claim 3, wherein said circumferential side walls defined a closed perimeter of said enclosure in said open and closed positions of said lid such that said absorbent articles cannot be slid out of said body and are removed by the user by pulling on said uppermost article in a direction generally transverse to a plane of said opening.

5. The absorbent article carrying case as in claim 1, wherein said lid is pivotal relative to said body.

6. The absorbent article carrying case as in claim 1, wherein said lid is slidable relative to said body.

7. The absorbent article carrying case as in claim 1, wherein said body comprises a shape generally conforming to an outline of said absorbent articles carried therein.

8. The absorbent article carrying case as in claim 1, wherein said push structure comprises an access opening defined through a wall of said body, said access opening having a restricted size so as to prevent removal of said bottommost article through said access opening.

9. The absorbent article carrying case as in claim 8, wherein said access opening is covered by an elastic material.

10. The absorbent article carrying case as in claim 9, wherein said elastic material is translucent.

11. The absorbent article carrying case as in claim 1, wherein said push structure comprises a resilient portion of a wall of said body generally opposite from said opening.

12. The absorbent article carrying case as in claim 1, wherein said body further comprises a viewing window such for a user to ascertain the contents of said body without opening said lid.

13. The absorbent article carrying case as in claim 12, wherein said viewing window is incorporated with said push structure.

14. The absorbent article carrying case as in claim 1, further comprising a biasing structure configured with said body to bias said stacked absorbent articles generally away from said opening and towards said push structure.

15. The absorbent article carrying case as in claim 14, wherein said biasing structure comprises a detent formed in a front wall of said body and said push structure is defined in a back wall of said structure.

16. The absorbent article carrying case as in claim 1, wherein said lid defines at least a portion of a front wall of said body in said closed position such that said opening is defined in said front wall upon said lid being moved to said open position.

17. The absorbent article carrying case as in claim 1, further comprising a stack of said personal care absorbent articles carried in said body.

18. The absorbent article carrying case as in claim 17, wherein said personal care absorbent articles comprise one of sanitary napkins, pantiliners, tampons, and interlabial devices.

19. A portable carrying case for personal care absorbent articles, comprising:
- an elongated body having a front wall, back wall, and side walls, said body defining an internal enclosure within said walls, said body configured with an exterior surface that is ergonomically shaped to generally conform to being carried and held in one hand of the user while the user's other hand removes an article from the internal enclosure;
- a stack of personal care absorbent articles carried in said enclosure;
- an opening defined in at least a portion of said front wall body at a location so as to expose an upper one of said absorbent articles for dispensing through said opening without generally exposing underlying absorbent articles;
- said side walls defining a closed perimeter around said opening such that said absorbent articles are prevented from being slid out of said enclosure;
- a lid movably disposed relative to said body from a closed position wherein said opening is covered by said lid to an open position wherein access is provided to said absorbent articles through said opening;
- a manual push structure defined in said back wall and configured to allow a user to push on the bottommost one of said stacked absorbent articles so as to move the uppermost one of said stack of absorbent articles towards said opening for grasping and retrieval by the user in a direction generally transverse to a plane of said front wall; and
- a biasing structure configured with said body and disposed to bias said stack of absorbent articles towards said back wall.

20. The absorbent article carrying case as in claim 19, wherein said lid is pivotal relative to said body.

21. The absorbent article carrying case as in claim 19, wherein said lid is slidable relative to said body.

22. The absorbent article carrying case as in claim 19, wherein said body comprises a shape generally conforming to an outline of said absorbent articles carried therein.

23. The absorbent article carrying case as in claim 19, wherein said push structure comprises an access opening defined through said back wall, said access opening having a restricted size so as to prevent removal of said bottommost article through said access opening.

24. The absorbent article carrying case as in claim 23, wherein said access opening is covered by an elastic material.

25. The absorbent article carrying case as in claim 24, wherein said elastic material is translucent.

26. The absorbent article carrying case as in claim 19, wherein said push structure comprises a resilient portion of said back wall generally opposite from said opening.

27. The absorbent article carrying case as in claim 19, wherein said body further comprises a viewing window such for a user to ascertain the contents of said body without opening said lid.

28. The absorbent article carrying case as in claim 27, wherein said viewing window is incorporated with said push structure.

29. The absorbent article carrying case as in claim 19, wherein said biasing structure comprises a detent formed in said front wall of said body.

30. The absorbent article carrying case as in claim 29, wherein said lid defines at least a portion of a front wall of said body in said closed position such that said opening is defined in said front wall upon said lid being moved to said open position, said detent formed in said lid.

31. The absorbent article carrying case as in claim 30, wherein said personal care absorbent articles comprise one of sanitary napkins, pantiliners, tampons, and interlabial devices.

* * * * *